United States Patent [19]

Barbaret et al.

[11] Patent Number: Plant 6,270

[45] Date of Patent: Sep. 6, 1988

[54] CARNATION PLANT NAMED 'LONGUMO'

[75] Inventors: Nicole Barbaret; Yves Ducloux, both of Antibes, France

[73] Assignee: Laboratoire de Physiologie Vegetale de la Londe, La Londe, France

[21] Appl. No.: 889,509

[22] Filed: Jul. 25, 1986

[51] Int. Cl.[4] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new spray carnation variety having relatively small blooms of a generally orange yellow coloration grown in clusters on relatively short, straight, upright stems and produced profusely in recurrent blooming periods during the course of the blooming season, the plant itself having a vigorous, upright and rather rigid growing habit reaching a height averaging about 93 cm. at eight months with rather abundant foliage.

1 Drawing Sheet

BACKGROUND OF THE NEW PLANT

This new carnation variety originated as a natural mutation or sport of the carnation variety 'Lonforem' (U.S. Plant Pat. No. 5,444) discovered in the course of our inspection of a field of the parent plant being grown for commercial purposes at La Londe, Les Maures, France. The bright orange yellow color of the blossoms of this sport caused us to asexually reproduce the sport for test purposes and this was done at La Londe by means of cuttings with results so satisfactory that we directed that the resulting plants be grown through several successive generations by means of cuttings from the next preceding growth with the result that the distinctive and novel characteristics of the original sport held true from generation to generation and appeared to be firmly fixed.

DESCRIPTION OF THE DRAWING

This variety of our new spray carnation is illustrated by the accompanying photographic drawing which shows, in full color, the upper portion of a typical spray stem bearing buds at various stages of opening together with flowers in several stages of maturity, the colors shown being as nearly true to those specified herein as is reasonably possible to obtain by conventional photographic procedures.

DESCRIPTION OF THE NEW PLANT

The following is a detailed description of our new carnation plant based upon observations of greenhouse grown plants made at La Londe, Les Maures, France, in early 1986, the color designations being according to The R.H.S. Colour Chart published by The Royal Horticultural Society of London, England.

THE PLANT

Origin: Sport.
Parentage: 'Lonforem', U.S. Plant Pat. No. 5,444.
Classification:
- *Botanic.*—*Dianthus caryophyllus.*
- *Commercial.*—Spray carnation.

Form: A tall bush of erect spray shape having at least four stems emitted from a main stem near the ground.
Height: About 93 cm., in average, at eight months.
Main stem:
- *Length.*—Less than 15 cm. due to pinching.

Branching character: Alternate.
Growth: Vigorous, upright and rather rigid.
Foliage:
- *Quantity.*—Rather abundant.
- *Number of leaves.*—More than 120.
- *Size of leaf.*—About 6.7 cm. long and 0.8 cm. wide at the seventh node.
- *Leaf shape.*—Lineal with acute apex and curved margins.
- *Texture.*—Leathery.
- *Color.*—Upper side — 191A. Under side — 191A.
- *Leaflets.*—None.
- *Ribs, Veins and Rachis.*—Hardly noticeable.

THE BUD

Size: Medium.
- *Diameter.*—About 1.3 cm.
- *Length.*—About 2.7 cm.

Form: Generally cylindrical or oblong in shape.
Color of petals:
- *When sepals first divide.*—Barium yellow.
- *When petals begin to unfurl.*—Saffron yellow.

Sepals:
- *Number.*—Five. The sepals are hooded over the bud before dividing and stand up as the flower petals unfurl.
- *Shape.*—The sepals are joined together at the lower part and otherwise are generally ovate with a somewhat scuminate tip.
- *Color.*—Inside — 145D. Outside — 144C/137D.
- *Striae.*—Longitudinal.

Calyx:
- *Shape.*—Cylindrical and narrow.
- *Size.*—Medium.
- *Aspect.*—Smooth.
- *Splitting.*—The calyx does not split.

Flower stem:
- *Length.*—About 46.6 cm., in average.
- *Character.*—Erect and rather thin.
- *Color.*—191A.

THE FLOWER

Blooming habit: Recurrent and profusely during the course of the blooming season with a tendency to five fewer blooms in the fall.
Size of bloom: Small.
- *Diameter.*—Averaging about 5 cm.

*Depth.*—Averaging about 4.4 cm.

Borne: As a cluster with more than three flowers per stem.

Shape: High centered when the bloom first opens and dome shaped as the bloom matures.

Petalage:

*Number of petals.*—About 26, in average.

*Arrangement.*—Imbricated.

*Form.*—Fan shaped with serrated outer end edges.

*Texture.*—Soft.

*Appearance.*—Satiny.

*Color.*—Both inside and outside petals: Upper side: Body — Generally 19B with 10C and 12C toward the petal base and occasionally streaked with 46B at the outer margins. Base — Greenish yellow. Reverse side: 10D and 12D.

Petaloids:

*Number.*—Less than four.

*Size.*—Smaller than the petals.

*Color.*—Same as the petals.

Flower stem:

*Average length.*—46.6 cm., cut at the tenth node.

*Color.*—191A.

*Character.*—Upright and with good strength.

Fragrance: Perceptible

Persistence: The flowers hang on and dry

Disease resistance: Resistant to *Fusarium oxysporum* as observed I.N.R.A. Antibes, France.

Lasting quality:

*As a cut flower.*—At least 10 days in vase keeping.

REPRODUCTIVE ORGANS

Stamens:

*Number.*—1 to 6.

*Arrangement.*—Around the ovary.

*Anthers.*—Size: Less than 4 mm. Color: White

*Filaments.*—Average length: About 2 cm. Color: Whitish

Pistils:

*Number.*—Two

*Styles.*—Average length: About 2.9 cm. Color: Yellowish white.

*Stigmas.*—Color: Yellowish white and lightly pinkish.

Character of ovaries: Spherical and lightly ribbed.

This carnation variety differs from the parent 'Lonforem' by having a clear orange yellow color of the flower petals. Otherwise, this new variety retains the plant characteristics of the parent variety.

We claim:

1. The new and distinct variety of spray carnation, substantially as herein shown and described, characterized by the generally orange yellow overall coloration of the flower in full bloom, its profuse but recurrent flower production during the blooming season, and its vigorous, upright growth habit reaching a height of about 93 cm. with flower stems of about 46.6 cm. in length.

* * * * *

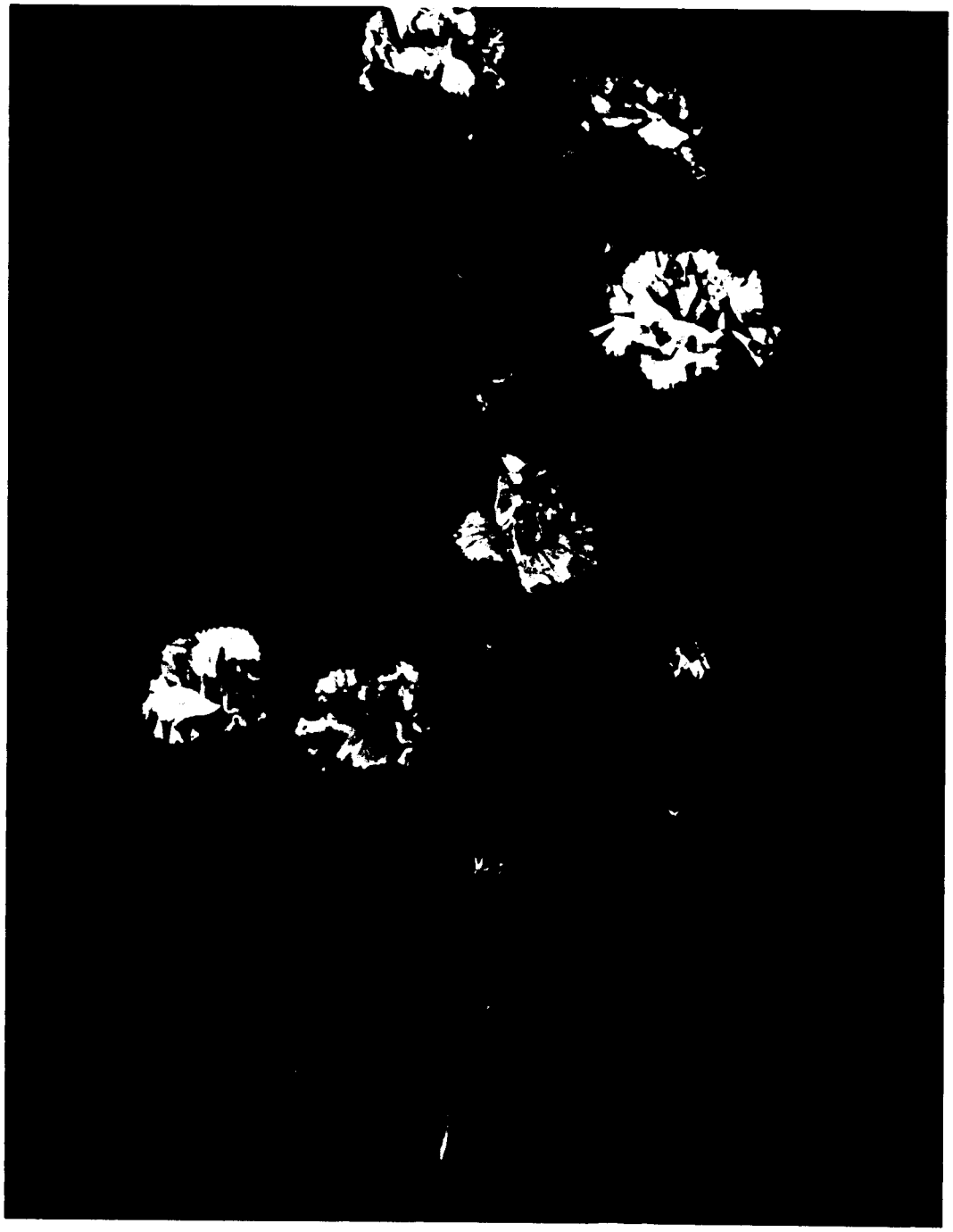
ok to print
7/26/88
kem